(12) United States Patent
Ekanayake et al.

(10) Patent No.: US 7,303,773 B2
(45) Date of Patent: Dec. 4, 2007

(54) PROCESS FOR ENRICHING EXTRACTS OF NATURAL THEANINE

(75) Inventors: Athula Ekanayake, Cincinnati, OH (US); Jianjun Justin Li, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 469 days.

(21) Appl. No.: 10/689,910

(22) Filed: Oct. 21, 2003

(65) Prior Publication Data

US 2005/0084544 A1 Apr. 21, 2005

(51) Int. Cl.
*A01N 65/00* (2006.01)
*C07D 473/00* (2006.01)

(52) U.S. Cl. ........................ 424/729; 424/774; 544/276

(58) Field of Classification Search ................. 424/729
See application file for complete search history.

(56) References Cited

U.S. PATENT DOCUMENTS

| | | | |
|---|---|---|---|
| 5,141,611 A * | 8/1992 | Ford | |
| 5,280,901 A | 1/1994 | Smith et al. | |
| 5,879,733 A | 3/1999 | Ekanayake et al. | |
| 5,997,929 A | 12/1999 | Heeb et al. | |
| 6,210,679 B1 * | 4/2001 | Bailey et al. | |
| 2001/0001307 A1 * | 5/2001 | Ueda et al. | |
| 2002/0058092 A1 | 5/2002 | Kattenberg et al. | |

FOREIGN PATENT DOCUMENTS

| | | |
|---|---|---|
| EP | 0 847 697 | 6/1998 |
| EP | 1 057 483 | 12/2000 |
| EP | 1 077 211 | 2/2002 |
| JP | 10184143 | 6/1998 |
| JP | 11056243 | 3/1999 |
| JP | 2003111558 | 4/2003 |
| JP | 2004010545 | 1/2004 |

OTHER PUBLICATIONS

Zhongyu, Liu et al. Journal of Xiamen University, (Sep. 1999), 38(5): 716-720. IR absorption spectra of tea polyphenol extracted by PA/SiO2.*
Kubota, E. et al., JEOL News (1973), 11A(s): 16-21. A quantitative determination of amino acids in tea by an automatic amino acid analyser.) in view of Ford (A*, US 5,141,611).*

* cited by examiner

*Primary Examiner*—Michele Flood
(74) *Attorney, Agent, or Firm*—Ingrid N. Hackett; S. Robert Chuey; Kim W. Zerby

(57) ABSTRACT

A process for enhancing theanine extraction from plant material through a series of extraction, adsorption and filtration steps. More specifically, disclosed is a process for isolating theanine from a plant material, which includes the steps of: a) contacting the plant material with a solvent to obtain an extract comprising theanine; b) contacting the theanine extract with an adsorbent to obtain a theanine-containing eluate; and c) subjecting the theanine eluate to a filtration step to obtain a theanine-rich extract.

6 Claims, No Drawings

PROCESS FOR ENRICHING EXTRACTS OF NATURAL THEANINE

FIELD OF THE INVENTION

The present invention relates to a process for producing enriched extractions of natural theanine from plant material.

BACKGROUND

Theanine, or 5-N-ethyl glutamine, is a non-protein amino acid. Theanine is rare in nature, being most commonly found in tea leaves (*Camellia sinesis*) and other species of Camellia, as well as edible bay boletes mushrooms (*Xerocomus badius*). It is found to the extent of about 2% by dry weight in the leaves of the tea plants. In tea extracts, it is usually found closely associated with the phenolic fraction, and is generally believed to modify the astringency of tea polyphenols.

Recently, theanine has been investigated and has been found to be increasingly associated with therapeutic benefits in the areas of cardiovascular health and cancer treatment. Specifically, theanine has been found to help lower blood pressure and enhance the effects of chemotherapeutic agents. Theanine also has a reputation for promoting mental and physical relaxation, and decreasing stress and anxiety without inducing drowsiness. Therefore, there is a need to develop a more effective method for extracting theanine from plant material, which can then be incorporated into various foods, beverages, supplements and the like, to provide added therapeutic value.

Applicants have surprisingly discovered that, by using the process disclosed herein, the theanine yield is enhanced. Namely, the process of the present invention allows for the production of an increased amount of theanine. Current tea processes use relatively simple solubility-based methods of theanine extraction from waste tea materials. As a result, current natural theanine preparations generally contain only 20-30% theanine. Moreover, theanine is typically not capable of being efficiently separated from preparations containing polyphenols. The present inventors have surprisingly discovered that, by separating the polyphenolic constituents from the theanine by use of adsorbent materials, as described herein, the resulting theanine-rich extract contains at least about 2 times the concentration of the starting composition based on the Brix measurement.

SUMMARY OF THE INVENTION

In one aspect, the present invention relates to a process for isolating theanine from a plant material, comprising: a) contacting the plant material with a solvent to obtain an extract comprising theanine; b) contacting the theanine extract with an adsorbent to obtain a theanine-containing eluate; and c) subjecting the theanine-containing eluate to a filtration step to obtain a theanine-rich extract. Additionally, after the theanine eluate is subjected to the filtration step, the resulting theanine-rich extract can optionally be concentrated via ion exchange chromatography, or any other concentration technique known to those skilled in the art.

In another aspect of the present invention, the present process may be used to supplement other tea processing methods. In this embodiment, materials otherwise discarded as waste products in tea processing are subject to the processes of the present invention to provide a useful theanine-rich extract. In this case, a tea extract may be subjected to a microfiltration step, and optionally, a subsequent nanofiltration or ultrafiltration step, after the foregoing extraction step (a), but prior to the foregoing adsorbent step (b). The theanine-containing retentates resulting from these initial filtration steps may then be combined and contacted with an adsorbent, subjected to filtration, and optionally concentrated, to obtain a theanine-rich extract.

DETAILED DESCRIPTION OF THE INVENTION

A. Definitions

As used herein, the term "comprising" means various components and processing steps can be cojointly employed in the products and processes of the present invention. Accordingly, the term "comprising" encompasses the more restrictive terms "consisting essentially of" and "consisting of."

As used herein, the terms "extract comprising theanine" and "theanine extract" are used interchangeably to refer to the product of the initial extraction step, as described herein.

As used herein, the term "filtration" is used to refer to either ultrafiltration or nanofiltration. In general, the "permeate" is the component that passes freely through the filter, while the "retentate" is the component that is retained by the filter. When processing tea for purposes other than to collect theanine, the retentates, rather than the permeates, are used as a source of theanine.

As used herein, the term "microfiltration" refers to processes that use filtration membranes having larger pore size than both ultrafiltration and nanofiltration. Microfiltration involves subjecting the theanine extract or eluate to filtration through a filter having a pore size of less than about 0.45 µm.

As used herein, the term "nanofiltration" refers to processes that use filtration membranes having a smaller molecular weight or pore size than those typically used in ultrafiltration processes. Like ultrafiltration, nanofiltration rejects a portion of the extract or eluate components above a certain molecular size while allowing those of a smaller size to pass through. Suitable nanofiltration membranes for use in the process of the present invention are preferably made from polymers having a nominal molecular weight cut off of from about 700 to about 5000 Daltons (corresponding to pore sizes in the range of from about 17 to about 40 Angstroms). Particularly preferred nanofiltration membranes are made from polymers having a nominal molecular weight cut off of from about 800 to about 2000 Daltons (corresponding to pore sizes in the range of from about 18 to about 27 Angstroms). This pore size, in general, allows unoxidized phenolic compounds to pass through the membrane while retaining oxidized phenolic compounds.

As used herein, the term "plant material" means species of *Camellia*, preferably tea leaves (*Camellia sinesis*), as well as edible bay boletes mushrooms (*Xerocomus badius*) and any other natural source of theanine known to those skilled in the art.

As used herein, the term "secondary amino acids" is meant to encompass both protein and non-protein amino acids, other than theanine, found in the plant material.

As used herein, the term "substantially free" means that after contacting the theanine extract with an adsorbent, the total polyphenol content in the resulting theanine-containing eluate is reduced by at least about 70%, preferably by at least about 80% and more preferably at least about 88%. Total polyphenols are determined by using the method of V. L. Singleton and J. A. Rossi as described in "*Colorimetry of*

*total phenolics with phophomolybdic-phosphotungstic acid reagents.*" American Journal of Enology and Viticulture, 3, 144-158 (1965).

As used herein, the terms "theanine-containing eluate," "theanine eluate" and are used interchangeably to refer to the desired theanine-containing component collected after exposure to the adsorbent as described herein. Such adsorption step may be column adsorption, or any other adsorption means known to those having ordinary skill in the art.

As used herein, the term "theanine-rich extract" means an extract having a theanine concentration of at least about 2 times, and preferably at least about 2.5 times, the starting composition based on the Brix measurement, i.e. Theanine/Brix. This concentration is determined by using the method of H. Godel, P. Seitz and M. Verhoef, which is discussed in "*Automated amino acid analysis using combined OPA and FMOC-CI percolumn derivatization.*" LC.GC International, 5(2), 44-49 (1992). Moreover, the theanine-rich extract described herein is substantially free of polyphenols.

As used herein, the term "theanine-containing retentate" means the theanine-containing components remaining on the upstream side of the filter after ultrafiltration or nanofiltration. Such theanine-containing retentates are used as the source of theanine when the focus of tea processing is not to collect theanine, but instead is the production of the tea-containing composition itself (e.g., where a tea composition having high catechin levels is desired).

As used herein, the term "ultrafiltration" means a filtration method that uses an open filtration membrane with a pore size capable of allowing through molecules from at least about 10,000 to at least about 100,000 Daltons in molecular weight. Typically, ultrafiltration removes large molecular weight polysaccharides and proteins, but not oxidized phenolics.

As used herein, the term "water," means any of deionized water, reverse osmosis water, distilled water, or mixtures thereof, however, deionized water is preferred.

All amounts, parts, ratios and percentages used herein are by weight unless otherwise specified.

B. Process

The present invention relates to a process for enriching the amount of the non-protein amino acid theanine derived from a plant material.

1. Initial Extraction of Theanine from Plant Material

The first step of the present process involves contacting the plant material with a solvent to obtain an extract comprising theanine. The plant material used in the present invention can be any of tea leaves (*Camellia sinesis*), other species of *Camellia*, edible bay boletes mushrooms (*Xerocomus badius*), or any other natural source of theanine known in the art. However, the plant material used herein is preferably tea leaves, and more preferably green tea leaves. The preferred extraction process involves steeping the tea leaves in hot water. The tea leaves are extracted using hot water, from about 70-100° C. (from about 158-212° F.), preferably from about 75-90° C. (from about 167-194° F.), and more preferably from about 80-85° C. (from about 176-185° F.), and a combined tea leaf:water ratio of about 1:15 to about 1:20, i.e. for every 1 kg of tea leaves used, about 15 to 20 kg of hot water is used. The tea leaves are soaked in the hot water for about 30 to 45 minutes, after which the wet leaves are filtered out through one or more layers of muslin cloth, or other similar straining material, and the theanine extract is collected. The wet leaves may then be re-extracted with another volume of hot water and soaked for about 30 to 45 minutes further. The leaves are again filtered out and the theanine extract collected. The two theanine extracts are then combined and are ready for further processing. See, for example, U.S. Pat. No. 5,879,733 (Ekanayake et al.), issued Mar. 9, 1999, which discloses suitable extraction procedures.

2. Exposing Extract to Adsorbent

In one embodiment, the theanine extract resulting from the previous step is subsequently exposed to an adsorbent, which separates the theanine and secondary amino acids from other associated substances, such as polyphenols, pectins, and proteins. The result is a theanine-containing eluate that is substantially free of the aforementioned associated polyphenols. The preferred method of carrying out this adsorption step is column chromatography. However, any similar method of separation commonly known to those skilled in the art is acceptable. For example, the theanine extract and adsorbent may be combined in a solvent medium and mixed thoroughly.

As aforementioned, column chromatography is preferably used to separate the theanine from the other components in the theanine extract. To separate via column chromatography an inert column, preferably made of glass or plastic, is first packed with an adsorbent or column packing. The adsorbent material may be any of a variety of hydrophobic cationic materials, however, polymeric resins, such as polyamides, polyvinylpolypyrollidine, polyvinylpyrollidine, or Polyclar® is preferred. The column is then equilibrated with a solvent that is preferably water-soluble and does not form two phases when mixed with water. The solvent utilized in this phase of the process is preferably selected from water, ethanol, propylene glycol, glycerin, weak solutions of acetone, propanols, other like alcohols, and mixtures thereof. More preferably, the solvent comprises a mixture of water and ethanol. Still more preferably, the solvent mixture comprises less than about 80%, preferably less than about 40% and more preferably less than about 20% ethanol, by weight of the solvent. In an alternate embodiment, the solvent comprises water.

Next, the theanine extract is pumped through the column and the components that are not adsorbed, or poorly adsorbed, i.e. theanine, will be the first components to elute with the solvent. As the solvent strength is increased, such as, for example, through the addition of more ethanol, more strongly adsorbed components are released from the adsorbent material in the column and elute with the solvent. This process allows for the separation of the desired materials and the production of a theanine-containing eluate.

3. Filtration of the Theanine-Containing Eluate

The theanine-containing eluate is then subjected to a filtration step, to remove additional high molecular weight material, such as polysaccharides, pectins and proteins, and further enrich the theanine concentration of the eluate. As defined above, this filtration step may be either ultrafiltration or nanofiltration. Each of these filtration processes is set forth below.

Nanofiltration involves contacting the theanine eluate with a nanofiltration membrane to provide a filtered theanine-rich extract. Nanofiltration according to the present invention removes the higher molecular weight materials such as polysaccharides, pectins and proteins.

It is preferred that the nanofiltration step be carried out while the theanine eluate is at a temperature of from about 30° C. to about 50° C. (about 86° F. to about 122° F.), preferably from about 35° C. to about 50° C. (about 95° F. to about 122° F.), and more preferably from about 45° C. to about 50° C. (about 113° F. to about 122° F.). This avoids the formation of 'tea cream.' Tea cream is a hot soluble complex of caffeine, phenolics and other high molecular weight materials such as polysaccharides. It is found to a large extent in black tea extracts and to a much lesser extent in green tea extracts. However, it is beneficial to avoid the formation of tea cream to ensure efficient filtration.

Efficient nanofiltration is typically achieved by warming the theanine eluate after exposure to the adsorbent material and just prior to nanofiltration. Carrying out this nanofiltration step while the theanine eluate is within this temperature range is beneficial in two respects. If the temperature is substantially below about 37° C. (100° F.), desired amino acids, such as, theanine, can complex with remaining oxidized polyphenols to form larger molecules that are then removed by the membrane during nanofiltration of the theanine eluate. Conversely, if the temperature of the theanine eluate is much above about 60° C. (140° F.), more of the complexed oxidized materials in the theanine eluate can form, due to oxidation and other complexing reactions.

The pressure at which nanofiltration is carried out is another factor to consider in the process of the present invention. The pressure at which nanofiltration is carried out is preferably sufficiently high to provide adequate flow of the theanine eluate through the membrane to achieve the desired processing. However, the pressure is preferably not so high as to remove substantial amounts of water from the system, i.e. excessive concentration is preferably avoided. Typically, nanofiltration according to the present invention is carried out under a hydrostatic pressure of from about 100 psi to about 300 psi, preferably from about 175 psi to about 250 psi, applied to the upstream side of the membrane.

Suitable nanofiltration membranes for use in the process of the present invention are made from polymers having a nominal molecular weight cut off of from about 700 to about 5000 Daltons (corresponding to pore sizes in the range of from about 17 to about 40 Angstroms). Preferred nanofiltration membranes are made from polymers having a nominal molecular weight cut off of from about 800 to about 2000 Daltons (corresponding to pore sizes in the range of from about 18 to about 27 Angstroms). By use of a membrane having the appropriate nominal molecular weight cut off or pore size, the desired components in the theanine eluate of a molecular size smaller than the nominal pore diameter of the membrane, along with a large quantity of water (known as the permeate), are thus forced through the membrane and accumulate on the downstream side, while the undesired molecules of a molecular size larger than the nominal pore diameter of the membrane (known as the retentate), are rejected by the membrane and remain on the upstream side thereof.

The type of polymers used in making the nanofiltration membrane is also a factor in the process of the present invention. Suitable polymers are those that have less affinity for the desired components in the theanine eluate (i.e. theanine). Polymers such as cellulose acetates, polysulfones, polyvinylidenefluorides, and the like are usually suitable for making these nanofiltration membranes.

If the theanine eluate is subjected to nanofiltration, it is desirable to cool the resulting theanine-rich extract. As noted previously, the theanine eluate is typically warmed prior to nanofiltration. Typically, the resulting theanine-rich extract is cooled to a temperature of about 16° C. (60° F.) or less, preferably about 7° C. (45° F.) or less.

Over time, the nanofiltration membrane may become clogged with ever increasing amounts of higher molecular weight components that have been removed and retained. This is typically evidenced by a reduction in the flow rate of the permeate. Also, as the membrane becomes clogged, its processing efficiency decreases. Accordingly, the nanofiltration membrane can be periodically cleaned or replaced to maintain process efficiency and to ensure that undesired higher molecular weight components in the theanine eluate are removed to an adequate degree.

Similar to nanofiltration, ultrafiltration involves contacting the theanine eluate with an ultrafiltration membrane to provide a filtered theanine-rich extract. Ultrafiltration uses an open filtration membrane with a pore size capable of allowing through molecules from at least about 10,000 to at least about 100,000 Daltons in molecular weight. Ultrafiltration according to the present invention removes the mid-molecular weight materials such as the large molecular weight polysaccharides and proteins, but generally not oxidized phenolics.

When utilizing ultrafiltration, the theanine eluate can generally be filtered at a temperature of from about 30° C. to about 50° C. (about 86° F. to about 122° F.), preferably from about 35° C. to about 50° C. (about 95° F. to about 122° F.), and more preferably from about 45° C. to about 50° C. (about 113° F. to about 122° F.). Again, this temperature helps avoid the formation of 'tea cream' as described previously. Remaining conditions and equipment needed for ultrafiltration are the same as those described above for nanofiltration.

4. Optional Steps for Further Enrichment

Once the theanine eluate is subjected to one of the aforementioned filtration processes, the resulting theanine-rich extract can optionally be further enriched by subjecting it to further methods of concentration, including, but not limited to, ion exchange chromatography and electrodialysis. While many techniques are acceptable, ion exchange chromatography is preferred.

In ion exchange chromatography, charged substances are separated via column materials that carry an opposite charge. The ionic groups of exchanger columns are covalently bound to the matrix and are compensated by small concentrations of counter ions, which are present in the buffer. When a sample is added to the column, an exchange with the weakly bound counter ions takes place.

Ion exchange chromatography uses the fact that amino acids are multivalent anions or cations. Under strongly acidic pH conditions, amino acids are present as cations as a result of suppression of the dissociation of the carboxy group and protonation of the amino group. At pH values of about 12, amino acids are present as anions because the amino acid group is a free base and the carboxy group is dissociated. Due to the total charge (net charge) of the amino acids, it is possible to bind them to a corresponding, charged stationary phase, as long as the salt concentration is kept low.

During practical application of ion exchange chromatography it is beneficial to operate with pH values where the exchangers are mostly ionized and the biopolymers contain an excess of positive or negative charges, e.g. they are not near their p1 values (iso-electric point).

Excessively high salt concentrations may cause shielding of the charges on the amino acid surface such that effective binding to an exchanger can no longer take place. Since the bound molecules are subsequently displaced with the aid of an increasing salt gradient, amino acids of varying charge can be separated. The desorption of the amino acids from the column begins only with increasing salt concentrations or pH changes, when the amino acid loses charge. The substances that have a higher charge density, are bound correspondingly stronger to the column while others elute rapidly.

In the present invention, the ion exchange resin is first hydrated and any floating resin beads are removed so as not to block the column. The resulting resin slurry is then poured into a column, preferably made of glass or plastic, and packed well by passing 3 to 4 column volumes of water through the column. The column is then regenerated by passing through a solution of sodium chloride, hydrochloric acid, or the like, until the eluate turns from acidic to neutral or vice versa. The column is again washed with 3 to 4 column volumes of water to remove excess acid or salt. The theanine-rich extract is made acidic, i.e. a pH of about 2-3, using, for example, hydrochloric acid, and passed through the column. After again washing to remove any acid or salt, the column is eluted with buffers of increasing pH. The further enhanced theanine-rich extracts are collected and concentrated.

Another acceptable method by which to further enhance the theanine is electrodialysis. Electrodialysis is an electromembrane process in which ions are transported through ion permeable membranes from one solution to another under the influence of a potential gradient. The electrical charges on the ions allow them to be driven through the membranes fabricated from ion exchange polymers. Applying a voltage between two end electrodes generates the potential field required for this. Since the membranes used in electrodialysis have the ability to selectively transport ions having positive or negative charge and reject ions of the opposite charge, electrodialysis is useful in the concentration, removal or separation of materials having opposing charges.

The ion permeable membranes used in electrodialysis are essentially sheets of ion-exchange resins. They usually also contain other polymers to improve mechanical strength and flexibility. The resin component of a cation-exchange membrane has negatively charged groups chemically attached to the polymer chains. Ions with a charge opposite to the fixed charge are freely exchanged at these sites. The concentration of counter ions is relatively high, therefore, counter ions carry most of the electric current through the membrane. The fixed charges attached to the polymer chains repel ions of the same charge, in this case anions. Since their concentration in the membrane is relatively low, anions carry only a small fraction of the electric current through a cation permeable membrane. Attachment of positive fixed charges to the polymer chains forms anion permeable membranes, which are selectively transport negative ions.

A further example of a suitable concentration process includes concentrating the theanine-rich extract to about one-tenth of its starting volume, cooling it to about 10° C. (about 50° F.), and adding two volumes of isopropanol. The theanine and other remaining amino acids precipitate from solution and can be further purified by recrystallization. See, Abelian et al., "A Novel Method of Production of Theanine by Immobilized Pseudomonas nitroreducens Cells.," *Bioscience Biotechnology and Biochemistry*, 57(3), 481-483 (1993).

5. Alternate Embodiment

In another embodiment of the present invention, a tea extract can be first subjected to a microfiltration step, followed by an optional nanofiltration or ultrafiltration step, and the resulting theanine-containing retentates combined, prior to contacting the retentates with an adsorbent. The parameters of the microfiltration and nanofiltration/ultrafiltration steps are the same in this alternate embodiment as discussed above, except that further theanine enrichment occurs using the retentates, rather than the permeates. This is because in this alternate embodiment, extracting theanine may not be the main focus of the process. This alternate embodiment is useful in tea processes where the theanine-containing retentate is considered 'waste' material, i.e. the purpose of the tea process is to obtain components from the tea other than theanine.

In one such embodiment, the tea extract is first subjected to a microfiltration step. Microfiltration involves contacting the tea extract with a microfiltration membrane having a pore size of less than about 0.45 μm and is conducted under the same temperature conditions as described in the nanofiltration explanation. However, unlike the other filtration processes, microfiltration should be conducted at a lower pressure, typically less than about 50 psi. The permeate passes through the filter for further processing while the retentate, which contains theanine, and was previously considered 'waste,' is retained.

After microfiltration, the permeate is optionally subjected to nanofiltration or ultrafiltration to separate other tea components found in the permeate. The theanine is again collected in the retentate.

Once the foregoing filtration steps are complete, the theanine-containing retentates are combined and the theanine content is then further enhanced and concentrated via adsorption, filtration and, optionally, concentration according to the methods previously discussed.

6. Using the Theanine-Rich Extract

After subjecting the plant material to one of the foregoing embodiments, the resulting theanine-rich extract may then be used to enhance the theanine concentration of foods and beverages, such as tea and tea extracts, preferably green tea and green tea extracts. Additionally, the theanine may be used in dietary supplements, and the like.

EXAMPLES

Example 1

Enhancing Theanine in Green Tea Leaf Extract by Using 'Waste' Materials

About 200 g of commercial process quality green tea leaves are extracted with about 1600 g of deionized water, at about 75-85° C. (about 167-186° F.) for approximately 45 minutes. The resulting slurry is filtered through two layers of muslin cloth and yields about 1200 g of crude tea extract. The residual leaves are re-extracted with deionized water under the foregoing conditions and again filtered through muslin cloth. The tea extracts are combined and subjected to microfiltration via a 0.45 μm pleated filter (1.5 ft$^2$, acrylic co-polymer on a polypropylene-polyester support.) The resulting permeate is then subjected to nanofiltration using a Millipore® 1000 Dalton Molecular Weight Cut Off (MWCO) filter. The resulting permeate is then used to produce a clarified tea extract with lighter color and reduced bitterness. The retentates from these filtrations, which contain theanine, are combined to yield a theanine-containing retentate with a volume of about 200 mL and about 9.8° Brix. This theanine extract has a theanine concentration of about 700 mg/L. The theanine extract is also viscous in consistency and is, therefore, diluted with deionized water in a 1:1 ratio, and used as feed in the next step.

Amberlite XAD 16HP® (Rohm & Haas) is packed in a column (2.5 cm ID×75 cm height) to give a column volume of about 350 mL. The column is washed with about 4-5 column volumes of deionized water. The diluted theanine extract from the foregoing extraction step is pumped into the column until breakthrough occurs (about 100 mL). The column is first eluted with deionized water to remove the non-phenolic materials including theanine and other polysaccharides. When the eluate gives no precipitate or a clouding reaction with ethanol, the water elution is stopped. This eluate contains about 257 mg/L theanine and about 6 mg/mL tea polysaccharides. It is then nanofiltered using a 1000 Dalton MWCO membrane to separate the high molecular weight non-phenolic materials from theanine. When the theanine-rich extract is concentrated back to the original solution value of about 9.8°Brix, it yields a theanine concentration of about 6500 mg/L, showing a concentration effect of greater than nine times. It is substantially devoid of tea polyphenols. The theanine-rich extract may be added to the clarified tea extract to enhance its theanine concentration, or alternately, the theanine-rich extract may be subjected to further cleanup by ion exchange chromatography.

Example 2

Enrichment Using Nanofiltration

Process quality green tea leaves are extracted with deionized water at about 45-55° C. (about 113-131° F.). The water to tea leaves ratio is about 25:1. This extraction is continued for about 1.5 hrs, and the resulting theanine extract is filtered using muslin cloth. The residual tea leaves are then extracted once more as described above, and this second theanine extract is removed by filtration using muslin cloth. The two theanine extracts are combined, and the theanine content in them is determined to be about 225 mg/L. This theanine extract is then pumped into a column containing polyamide-11 (ICN Biochemicals).

To prepare the column, polyamide is first suspended in deionized water and the floating particles are removed. It is then packed in a column (2.5 cm ID×75 cm height, 330 mL) and washed with about five column volumes of deionized water. The column is first eluted with water, and then the substantially polyphenol-free theanine eluate fractions are collected. These fractions are combined and subjected to nanofiltration using the 1000 Dalton MWCO membrane to separate the high molecular weight non-phenolic materials from theanine. The theanine-rich extract, which may also contain small molecular weight material, is concentrated under vacuum and subjected to cation exchange chromatography. The resulting theanine is enriched.

Example 3

Enrichment of Non-Tea-Leaf Plant Material Using Microfiltration and Nanofilration When using non-tea leaf plant material, the material is first blanched to prevent the oxidation of the endogenous phenolics and to denature the cell membranes so the soluble material is easily extracted. Blanching is done by gathering the plant material and subjecting it to a steaming or panning (repeatedly contacted with a hot metal surface to transfer heat into tissue) process to deactivate the enzymes and denature the cell membranes to make cell constituents leach out easily. Next, the plant material is extracted with hot water at about 80-85° C. (about 176-185° F.) at a plant tissue:water ratio of about 1:8. During this step, the plant material is either blended in the water or ground up and suspended with stirring in the water. This first extraction is carried on for about 45 minutes to about one hour and then the extract is filtered through muslin cloth. The residue is re-suspended in hot water at the same ratio described above, and re-extracted as before. A second extract is separated out using standard filtration techniques previously discussed. These two theanine extracts are then combined and subjected to a microfiltration step to remove particulate matter and reduce microbial counts. This microfiltered theanine extract is then treated in the same manner as the freshly made theanine extract given in Example 2, discussed above.

Example 4

Enrichment Using Nanofiltration

About 40 g of commercial process quality green tea leaves are extracted with about 320 g of deionized water at about 75-85° C. (about 167-186° F.) for about 45 minutes with stirring. The slurry is then filtered through two layers of muslin cloth to yield about 240 g of crude theanine extract. The residual leaf is re-extracted with 320 g of deionized water at about 75-85° C. for about 45 minutes. The slurry is again filtered through two layers of muslin cloth. The two theanine extracts are combined and subjected to filtration via a 0.45 μm pleated filter (1.5 ft$^2$, acrylic co-polymer on a polypropylene-polyester support). Next, about 350 mL of pre-washed Amberlite XAD 16HP® (Rohm & Haas) is added to 450 mL of the above-described theanine extract. The combination is slurried gently for about 30 minutes and the supernatant liquid is filtered out. The resulting theanine eluate is substantially free of phenolic compounds.

The theanine is further purified by subjecting this supernatant to a nanofiltration step using a 1000 Dalton MWCO membrane that separates the high molecular weight non-phenolic materials from the theanine. The resulting theanine-rich extract is concentrated and chilled to about 10° C. (about 50° F.). It is then mixed with two volumes of isopropanol. The resulting precipitated theanine and other amino acids are further purified by recrystallization.

Example 5

Enriching Theanine Using Ultrafiltration

About 120 g of commercial process quality green tea leaves are extracted with about 960 g of deionized water at about 75-85° C. (about 167-186° F.) for about 45 minutes with stirring. The slurry is then filtered through two layers of muslin cloth to yield about 720 g of crude theanine extract. The residual leaf is then re-extracted with about 960 g of deionized water at about 75-85° C. for about 45 minutes, and then filtered through two layers of muslin cloth. The two theanine extracts are combined and centrifuged for about 30 minutes at 10,000 rpm. The clear supernatant is then carefully decanted off of the centrifuge tubes. The resulting theanine extract is next subjected to chromatography on a polyamide column. Polyamide is first suspended in deionized water and the floating particles are removed. The polyamide is then packed in a 330 mL column (2.5 cm ID×75 cm height) and washed with about five column volumes of deionized water. After adsorbing the theanine extract on the polyamide column, the column is eluted with water, and the substantially polyphenol-free theanine eluate is collected. This theanine eluate, which may also contain other high molecular weight non-phenolic materials, such as polysaccharides and proteins, is then subjected to ultrafiltration using a membrane with a molecular weight cut off of about 10,000 Daltons. The resulting theanine-rich extract, which also may contain low molecular weight amino acids, is concentrated under vacuum, chilled to about 10° C. (about 50° F.) and mixed with two volumes of isopropanol. The precipitated theanine, and other amino acids, are further purified by recrystallization.

All document cited in the Detailed Description are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for isolating theanine from a plant material, comprising:
    a) contacting the plant material with a solvent to obtain an extract comprising theanine;
    b) contacting the extract comprising theanine with a polyamide adsorbent to obtain a theanine-containing eluate; and
    c) subjecting the theanine-containing eluate to a nanofiltration step to obtain a theanine-rich extracts;
    d) precipitating theanine from the extract of sten (c).

2. The process of claim 1 wherein the plant material comprises tea leaves.

3. The process of claim 2 wherein the solvent is selected from the group consisting of water, ethanol, and mixtures thereof.

4. The process of claim 3 wherein the solvent comprises less than 20% ethanol, by weight of the solvent.

5. The process of claim 3 wherein the solvent comprises water.

6. The process of Ciaim 1 wherein step b) is performed using column extraction.

* * * * *

UNITED STATES PATENT AND TRADEMARK OFFICE
CERTIFICATE OF CORRECTION

PATENT NO. : 7,303,773 B2 Page 1 of 1
APPLICATION NO. : 10/689910
DATED : December 4, 2007
INVENTOR(S) : Athula Ekanayake et al.

It is certified that error appears in the above-identified patent and that said Letters Patent is hereby corrected as shown below:

<u>Column 6</u>

Line 56, delete "p1" and insert -- pI --.

<u>Column 12</u>

Line 5, delete "extracts" and insert -- extract --.

Line 6, delete "sten" and insert -- step --.

Line 16, delete "Ciaim" and insert -- Claim --.

Signed and Sealed this

Twenty-second Day of July, 2008

JON W. DUDAS
*Director of the United States Patent and Trademark Office*